United States Patent
Smith et al.

[11] Patent Number: 5,620,568
[45] Date of Patent: Apr. 15, 1997

[54] EXTRACTIVE DISTILLATION OF PROPYLENE OXIDE USING PROPANOL

[75] Inventors: William A. Smith, Round Rock; Mark A. Mueller, Austin, both of Tex.

[73] Assignee: Texaco Chemical, Inc., White Plains, N.Y.

[21] Appl. No.: 659,975

[22] Filed: Jun. 3, 1996

[51] Int. Cl.$^6$ ............................ B01D 3/40; C07D 301/32
[52] U.S. Cl. ............................ 203/63; 203/14; 203/78; 203/84; 549/541
[58] Field of Search ..................... 203/63, 14, 78, 203/84; 549/541

[56] References Cited

U.S. PATENT DOCUMENTS

| | | | |
|---|---|---|---|
| 3,632,482 | 1/1972 | Hoory | 203/78 |
| 3,909,366 | 9/1975 | Schmidt et al. | 203/69 |
| 4,140,588 | 2/1979 | Schmidt | 203/92 |
| 4,369,096 | 1/1983 | Seifert et al. | 203/63 |
| 5,006,206 | 4/1991 | Shih et al. | 203/63 |
| 5,139,622 | 8/1992 | Marquis et al. | 203/64 |
| 5,154,804 | 10/1992 | Marquis et al. | 203/63 |
| 5,262,017 | 11/1993 | Meyer et al. | 203/65 |
| 5,340,446 | 8/1994 | Nelson et al. | 203/56 |
| 5,354,430 | 10/1994 | Culbreth, III et al. | 203/64 |
| 5,354,431 | 10/1994 | Taylor | 203/64 |
| 5,464,505 | 11/1995 | Peters et al. | 203/64 |

*Primary Examiner*—Virginia Manoharan
*Attorney, Agent, or Firm*—Henry H. Gibson; James L. Bailey; Harold J. Delhommer

[57] ABSTRACT

An extractive distillation agent of 1-propanol is fed to an extractive distillation column used for the distillation of propylene oxide contaminated with water, acetone and methanol to obtain an overhead distillate fraction of essentially anhydrous propylene oxide contaminated with reduced quantities of acetone and methanol, and a heavier bottoms distillation fraction containing substantially all of the 1-propanol, water and acetone, some of the methanol and heavier by-products of propylene oxide formed in the distillation column.

2 Claims, 1 Drawing Sheet

EXTRACTIVE DISTILLATION OF PROPYLENE OXIDE USING PROPANOL

BACKGROUND OF THE INVENTION

1. Technical Field of the Invention

This invention relates to the purification of propylene oxide. More particularly, this invention relates to a distillation process for removing contaminating quantities of impurities, including oxygen-containing impurities such as methanol, acetone and water from an impure propylene oxide feedstock. Still more particularly, this invention relates to a method wherein an impure propylene oxide feedstock containing oxygen-containing impurities, for example, from about 50 to 4,000 ppm of methanol, from about 0.01 to about 2 wt. % of water, and from about 0.01 to about 2 wt. % of acetone is purified in an extractive distillation column using 1-propanol as the extractive distillation agent.

2. Prior Art

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol, acetone and water are common contaminants for propylene oxide which are removed only with difficulty.

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent.

Hoorl and Newman U.S. Pat. No. 3,632,482 is directed to a propylene oxide recovery process by extractive distillation using an alcohol-ketone-hydrocarbon solvent. The invention relates to a method for the purification of crude propylene oxide contained in a mixture produced by the epoxidation of propylene with an organic hydroperoxide and calls for extractive distillation of the crude propylene oxide in a plurality of successive extractive distillation zones with the aid of a solvent mixture consisting essentially of hydrocarbons, alcohols, and/or ketones corresponding to the organic hydroperoxide employed in producing the propylene oxide. In the preferred embodiment of their invention, the extractive distillation agent is a recycle fraction from a three column distillation sequence wherein the bottoms from the third distillation column are flashed to obtain an overhead composed of hydrocarbons, alcohols and/or ketones which is recycled as an extractive distillation agent to the three distillation columns involved in the propylene oxide purification sequence.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50–55 that: "Propylene oxide, however, has a substantial solubility in water and is readily hydrolyzed to propylene glycol (PG) in the presence of large amounts of water"—i.e., in the reboiler section of the tower.

U.S. Pat. No. 3,578,568 discloses the use of glycols or glycol ethers in an extractive distillation to remove oxygen containing impurities such as acetone, acetaldehyde, and methanol. It is claimed that the concentration of the solvent in the vapor space in the extractive distillation zone of the distillation tower is preferably between 15 and 50 mole percent of the total vapor.

Shih et al. U.S. Pat. No. 5,000,825 discloses the purification of monoepoxides such as propylene oxide that are contaminated with oxygenated impurities such as water, low molecular weight alcohols, low molecular weight ketones, low molecular weigh aldehydes and the like by the extractive distillation of the contaminated monoepoxide using a lower glycol containing 2 to 4 carbon atoms. Examples of lower glycols that are given in the patent include ethylene glycol, 1,2-propane diol, 1,3-propane diol, 1,4-butane diol, 1,2-butane diol, 1,3-butane diol and 2,3-butane diol. It is stated that higher diols or higher glycol ethers do not provide sufficient selectivity for the removal of such impurities and are not included as the extractive distillation solvents suitable for use in the invention.

Meyer et al. U.S. Pat. No. 4,971,661 discloses the use of an aqueous acetone extraction to remove methanol from propylene oxide.

Meyer et al. point out that the presence of additional acetone (added to feed or solvent) serves as a buffer between the reboiler section and the balance of the tower. This is apparent if one looks at the normal boiling points (i.e., atmospheric pressure):

| Component | NBP (°C.) |
| --- | --- |
| Propylene Oxide (PO) | 34 |
| Acetone | 56 |
| Water | 100 |

The acetone serves as a buffer section in the tower between the PO and water (a high concentration of water is in the reboiler and a high concentration of PO is above the acetone buffer zone). The acetone buffer zone limits the contact of PO with a high concentration of water. It is apparent that the additional acetone makes its presence known in the reboiler as well as evidenced by lower reboiler temperatures. This also helps reduce PO to PG conversion as the reaction rate increases with increasing temperature. Any PO making its way to the reboiler will see a lower temperature, thus reducing its conversion to PG.

It is clear that the tower should be operated at as low a pressure as is practical to minimize PO loss.

Shih et al. U.S. Pat. No. 5,006,206 discloses a method for the separation of propylene oxide from hydrocarbon impurities using a mixture of t-butyl alcohol and water as an extractive distillation solvent.

In U.S. Pat. No. 5,129,996, Shih discloses a method for the separation of propylene oxide from hydrocarbon impurities using a glycol having 2 to 5 carbon atoms as an extractive distillation solvent.

Peters et al. U.S. Pat. No. 5,464,505 discloses a method for the separation of propylene oxide from impurities such as water, methanol and acetone using, as the extractive distillation solvent, propylene oxide adducts of oxyethylene glycols. The propylene oxide adducts of oxyethylene glycols form in situ in the extractive distillation tower by the reaction of propylene oxide with oxyethylene glycol extractive distillation agents.

As shown by the foregoing discussion of the prior art, the results heretofore obtained in the purification of propylene oxide by extractive distillation have not been entirely satisfactory, particularly in respect of the loss of propylene oxide by reaction with water, extractive distillation agents, etc., in the distillation tower.

SUMMARY OF THE INVENTION

It has been discovered in accordance with the present invention, that propylene oxide can be effectively separated from impurities such as water, acetone and methanol in an extractive distillation column with a significantly reduced loss of propylene oxide when the extractive distillation is conducted in the presence of 1-propanol as an extractive distillation agent.

SUMMARY OF THE INVENTION

For example, in accordance with the present invention, an impure propylene oxide feedstock contaminated with 0.01 to 2 wt. % of water, from about 50 to about 4,000 ppm of methanol and from about 0.01 to about 2 wt. % of acetone is charged to the lower half of an extractive distillation column containing at least about 10 theoretical plates and an extractive distillation agent consisting essentially of 1-propanol is charged to the tower at a point at least 4 stages above the impure propylene oxide feed point. Preferably, the extractive distillation tower will contain from about 30 to about 120 theoretical plates and the extractive distillation agent will be charged to the tower at a point of from 7 to 50 theoretical stages above the impure propylene oxide feed point. The extractive distillation agent is introduced into the extractive distillation column in the ratio of said feedstock to said extractive distillation agent of from about 1:1 to about 20:1, and more preferably 2:1 to 10:1, whereby a lower boiling distillate fraction is obtained consisting essentially of propylene oxide contaminated with significantly reduced amounts of water, methanol and acetone, such as about 5 to about 600 ppm of water, about 15 to 2,000 ppm of methanol and about 0.1 to about 100 ppm of acetone.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because the water present in the propylene oxide will tend to react with the propylene oxide to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a heavy distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone.

It has been surprisingly discovered in accordance with the present invention that substantially all of the water initially present in a contaminated propylene oxide feedstock can be removed therefrom when the propylene oxide feedstock is extractively distilled in the presence of an extractive distillation agent consisting essentially of 1-propanol.

More surprising is the discovery that there is a significant reduction in the quantity of propylene oxide adducts of the extractive distillation agent formed in situ in the extractive distillation tower by the reaction of propylene oxide with the extractive distillation agent when the extractive distillation agent is 1-propanol. Even more surprising is the discovery that lower reboiler temperatures of about 90° to about 140° C. can be used without adversely effecting distillation efficiency and that this, in turn, reduces the amount of propylene oxide that reacts with the extractive distillation agent in the lower part of the distillation column. As a consequence, less of the higher boiling fraction can be purged while effectively purging heavy by-products from the extractive distillation column. Propylene oxide is also lost to the process because of its inclusion in the purge stream of the higher boiling fraction. In accordance with the present invention, when the extractive distillation agent is 1-propanol, loss of propylene oxide is significantly reduced because there is a lesser reaction of the propylene oxide with 1-propanol and because less propylene oxide is included in the purge stream.

BRIEF DESCRIPTION OF THE DRAWING

In FIG. 1, for convenience, the present invention is illustrated in connection with a process wherein the propylene oxide is prepared by the epoxidation of propylene with tertiary butyl hydroperoxide in solution in tertiary butyl alcohol to provide a reaction product comprising propylene oxide and additional tertiary butyl alcohol.

DESCRIPTION OF THE PREFERRED EMBODIMENT

Figure 1:
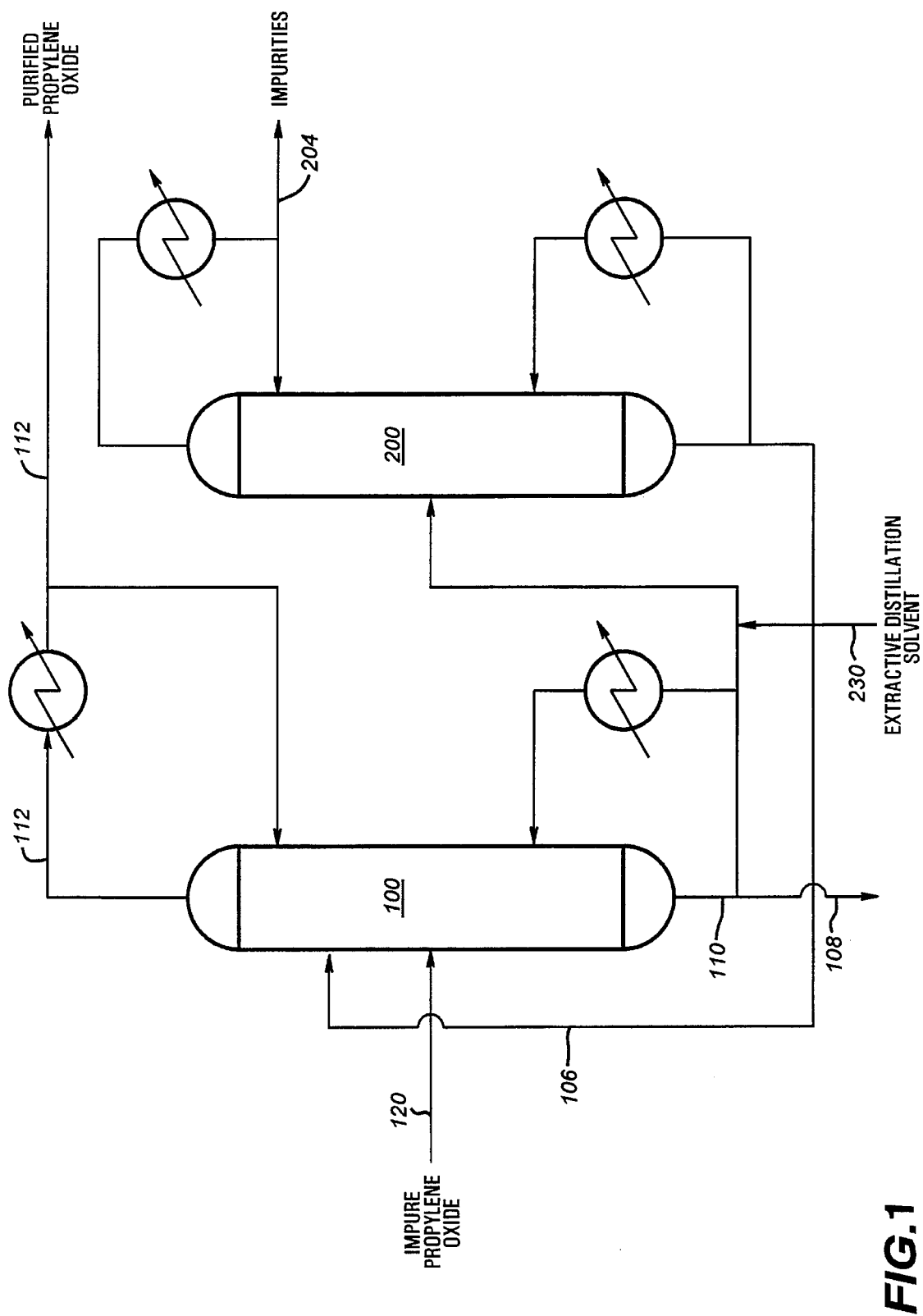
FIG. 1 is a schematic flow sheet with conventional parts omitted showing the general recovery sequence that is used in accordance with the present invention in purifying propylene oxide by extractive distillation using 1-propanol as the extractive distillation agent.

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, etc., have been omitted.

In accordance with a preferred embodiment of the present invention, propylene oxide is separated in a preliminary distillation zone (not shown) from other components of an epoxidation reaction mixture in order to provide an impure propylene oxide fraction contaminated with oxygen-containing impurities such as acetone, methanol, water, etc.

The impure propylene oxide feedstock that is thus obtained in the preliminary distillation zone is then purified in a propylene oxide purification distillation zone, which in accordance with the preferred embodiment of the present invention, comprises two distillation columns, each of which is equipped with an appropriate reflux condensing means and an appropriate reboiler heating means.

In accordance with the present invention, an impure propylene oxide fraction contaminated with from about 50 to about 4,000 ppm of methanol, from about 0.01 to about 2 wt. % of acetone and about 0.01 to about 2 wt. % of water and other oxygen-containing impurities is charged by way of a line 120 leading to a distillation column 100 which, in accordance with the present invention, will preferably be a column containing at least about 10 theoretical plates and more preferably, from about 30 to about 100 theoretical plates. The column 100 is suitably operated under distillation conditions including a pressure of about 10 to 40 psia, a reflux ratio of from about 2:1 to about 10:1, a reboiler temperature within the range of about 90° to about 140° C. and a top temperature of about 20° to about 80° C.

The impure propylene oxide is preferably charged to the distillation column 100 in the lower half thereof. An extractive distillation agent consisting essentially of 1-propanol is charged to the upper half of the distillation column 100 by an extractive distillation charge line 106.

Essentially anhydrous purified propylene oxide containing about 100 ppm or less of water is removed from the column 100 as a light distillation fraction 112, the purified propylene oxide in the line 112 containing significantly reduced amounts of methanol and acetone, such as about 15 to 900 ppm of methanol and about 0.1 to 100 ppm of acetone. A heavier fraction 110 is withdrawn from the distillation column 100 which contains substantially all of the extractive distillation agent charged by the line 106 and also substantially all of the water, acetone and other oxygen-containing impurities introduced into the column 100 with the impure propylene oxide 120.

The heavier distillation fraction 110 from the column 100 comprising water, methanol, acetone, tertiary butyl alcohol and other impurities and extractive distillation agent is charged to a second distillation column 200 wherein light impurities such as methanol, acetone, water, etc., are separated overhead as a distillation fraction 204 that is discharged from the system for any suitable use, such as for use as a steam boiler feedstock or for recovery. A purge stream is withdrawn by a line 108 to remove heavy by-products such as propylene oxide adducts of 1-propanol from the system. Propylene oxide present in purge line 108 is lost to the process.

In accordance with the present invention, fresh 1-propanol, either as the original charge, or as make-up solvent, is introduced into the system by a branch line 230 leading to the charge line 110 for the second distillation column 200 so that any water introduced into the system with the fresh 1-propanol will be separated therefrom in the column 200 and withdrawn from the column 200 through the line 204.

EXAMPLES

The invention will be further illustrated by the following specific examples which are given by way of illustration and not as limitations on the scope of this invention. Where parts are mentioned, they are parts by weight.

EXAMPLE 1

1-Propanol was screened in glassware distillation equipment for its effectiveness in removing water and methanol from crude PO. The procedure was to charge 750 g of crude PO to the pot of a 30 tray Oldershaw column equipped with a refrigerated condenser and a solvent feed point located 20 trays above the pot. The 1-propanol solvent was fed to the column at a rate of 50–60 g/hr (approximately the same as the overhead product rate) while boiling the PO up through the column at atmospheric pressure. After a 500 ml overhead sample was collected, it was analyzed by gas chromatography and for water by Karl Fischer. A comparison run was made without using any solvent. The results are as follows:

| Run Number | Solvent | Overhead Methanol (ppm) | Overhead Water (ppm) |
| --- | --- | --- | --- |
| 7299-20 | 1-propanol | 25.3 | 443 |
| 7299-26 | None | 65.9 | 404 |

1-Propanol improves the separation of methanol from crude PO as compared to simple distillation.

EXAMPLE 2

To a two-inch diameter 120 tray Oldershaw column was continuously fed 1.5 lb/hr of crude propylene oxide on tray 40 from the bottom and 0.25 lb/hr of triethylene glycol on tray 100 from the bottom. The column was operated at an 8 psig condenser pressure, an overhead temperature of 46° C. a reboiler temperature of 160° C. and a reflux rate of 3 lbs/hr. The overhead purified propylene oxide product contained, on average, 51 ppm water, 58 ppm methanol, 3 ppm propenal, and 0.2 ppm acetone. The bottoms stream contained the triethylene glycol solvent, approximately 40 wt. % heavies formed from the reaction of the solvent with propylene oxide, and 2.9 wt. % propylene oxide.

A comparison run was made under identical column operating conditions with 1-propanol as the solvent. However, the reboiler temperature was reduced to 108° C. since 1-propanol boils at a lower temperature than triethylene glycol. The overhead purified propylene oxide product contained, on average, 55 ppm water, 61 ppm methanol, 2 ppm propenal, and less than 0.1 ppm acetone. The bottoms stream contained the 1-propanol solvent, approximately 2 wt. % heavies formed from the reaction of the solvent with propylene oxide, and less than 0.2 wt. % propylene oxide.

1-Propanol removes impurities as effectively as triethylene glycol while reducing the losses of propylene oxide out the bottom of the column. In addition, the reaction of the 1-propanol solvent with propylene oxide is much reduced as compared to triethylene glycol.

Water and oxygen-containing impurities such as acetone and methanol are difficult to remove from propylene oxide by standard distillation. The use of extractive distillation columns with 1-propanol as the solvent improves the separation of these impurities from propylene oxide.

Having thus described our invention, what is claimed is:

1. An extractive distillation process for the distillation of impure propylene oxide in a distillation column to remove contaminants, including water, methanol and acetone, which comprises the steps of:

charging said impure propylene oxide feedstock to the lower half of a distillation column containing at least 25 theoretical plates, said impure propylene oxide feedstock comprising propylene oxide contaminated with from about 0.01 to 2 wt. % of water, from about 50 to about 4000 ppm of methanol and from about 0.01 to about 2 wt. % of acetone, introducing an extractive distillation agent consisting essentially of 1-propanol at a point at least 4 theoretical plates above said impure propylene oxide feed point, said extractive distillation agent being introduced into said distillation column in the ratio of said feedstock to said extractive distillation agent of from about 1:1 to about 20:1, withdrawing an overhead distillate fraction from said distillation column consisting of essentially anhydrous propylene oxide contaminated with reduced quantities of acetone and methanol, and withdrawing a bottoms distillation fraction from said distillation column containing substantially all of the 1-propanol, water and a portion of the acetone and a portion of the methanol introduced into said distillation column.

2. An extractive distillation process for the distillation of impure propylene oxide in a distillation column, which comprises the steps of:

introducing an impure propylene oxide feedstock into the lower half of a distillation column containing at least 25 theoretical plates, said impure propylene oxide feedstock comprising propylene oxide contaminated with from about 0.01 to about 2 wt. % of water, from about 50 to about 4000 ppm of methanol and from about 0.01 to about 2 wt. % of acetone, introducing an extractive distillation agent consisting essentially of 1-propanol at a point at least 4 theoretical plates above said impure propylene oxide feed point, said extractive distillation agent being introduced into said distillation column in the ratio of said feedstock to said extractive distillation agent of from about 1:1 to about 20:1, distilling said impure propylene oxide feedstock in said distillation column under distillation conditions including a pressure of about 10 to about 40 psia, a reflux ratio of from about 1:1 to about 5:1, and a reboiler temperature within the range of about 90° to about 140° C. and a top temperature of about 20° to about 80° C., whereby a reduced quantity of lighter boiling by-products will be formed, withdrawing an overhead purified propylene oxide distillate fraction from said distillation column consisting of essentially anhydrous propylene oxide, said purified propylene oxide distillate fraction being contaminated with reduced amounts of methanol and acetone, withdrawing a higher boiling distillation fraction from said distillation column containing a reduced amount of the propylene oxide charged to said distillation column and containing substantially all of the 1-propanol, water, and a portion of the methanol and a portion of the acetone introduced into said distillation column, and purging a portion of said higher boiling distillation fraction.

* * * * *